United States Patent [19]

Dunn

[11] Patent Number: 5,240,773

[45] Date of Patent: Aug. 31, 1993

[54] FABRIC REINFORCED THERMOPLASTIC RESINS

[75] Inventor: Edmund M. Dunn, Rydal, Pa.

[73] Assignee: Mutual Industries, Inc., Philadelphia, Pa.

[21] Appl. No.: 819,756

[22] Filed: Jan. 13, 1992

[51] Int. Cl.⁵ .................. C08L 27/12; C08F 259/06; B32B 9/00; B32B 7/00

[52] U.S. Cl. .................................. 428/408; 428/246; 428/902; 525/199; 525/239; 525/317; 525/318; 525/935

[58] Field of Search ............. 428/246, 408, 902; 525/199, 239, 317, 318, 935

[56] References Cited

U.S. PATENT DOCUMENTS

| | | | |
|---|---|---|---|
| 2,230,000 | 1/1941 | Hauff et al. | 525/239 |
| 3,992,725 | 11/1976 | Homsy | 428/408 |
| 4,610,101 | 9/1986 | Brown | 428/408 |
| 4,868,038 | 9/1989 | McCullough, Jr. et al. | 428/408 |

*Primary Examiner*—George F. Lesmes
*Assistant Examiner*—Kathryne E. Shelborne
*Attorney, Agent, or Firm*—John Lezday

[57] ABSTRACT

A fabric reinforced thermoplastic composite which is reformable at a temperature less than about 100° C. The thermoplastic comprises about 70 to 95% by weight of polyvinyl chloride and about 5 to 30% by weight of a halogenated polyvinyl chloride. The composite is used for forming orthotics and prosthesis devices.

11 Claims, 1 Drawing Sheet

FABRIC REINFORCED THERMOPLASTIC RESINS

FIELD OF THE INVENTION

The present invention relates to reformable fabric reinforced thermoplastic resin composites which can be used for orthotics and/or prosthesis devices. More particularly, there is provided a carbon or carbonaceous fabric reinforced polyvinyl chloride-halogenated polyvinyl chloride composite for use in prothesis devices and/or orthotics that is formable after immersion in hot water.

BACKGROUND OF THE INVENTION

Orthotic materials which are used in podiatry must be thin, lightweight, strong and durable. They must also be capable of being easily formed with low heat so as to be custom fitted by the podiatrist. Carbon fabric reinforced acrylic composite orthotics which are now commercially available have good compressive strength at a thickness of about 1.75 mm but are difficult to deform since the composite must be baked in a conventional over until it softens.

Orthotics prepared with thermoplastic resins are often preferred over orthotics prepared with thermosetting resins because composite articles prepared with thermoplastic orthotics can be easily post-formed and reshaped if defects are found whereas articles prepared with thermosetting orthotics cannot be reprocessed or reformed after cure. In the latter instance, the entire article must be scrapped if found defective. In addition, while orthotics prepared with thermoplastic resins have an almost infinite shelf life, prepregs prepared with thermosetting resins have a finite shelf life, usually no more than one year. Furthermore, when hot pressing the latter, extreme caution must be taken in effecting cure to ensure that the reaction proceeds at a proper rate since the amount of heat, heating time and pressure during cure are all extremely critical. No such caution is necessary in the case of thermoplastic orthotics as these materials do not undergo any cure.

Prosthesis devices must also be formable to permit adjustment from the initial fitting and over time when weight loss or gain of the patient affects proper fit.

U.S. Pat. No. 4,868,038 to McCullough et al, which is herein incorporated by reference discloses a composite material of synthetic resin which is reinforced with carbonaceous fibers. However, a composite which can be reformed at a temperature less than 100° C. is not disclosed.

U.S. Pat. No. 4,764,397 to Fischer et al, which is herewith incorporated by reference, discloses various processes which can be used to make the composites of the present invention. However, a composite comprising polyvinyl chloride and halogenated polyvinyl chloride is not disclosed.

SUMMARY OF THE INVENTION

The present invention provides a fabric reinforced composite which is reformable at a temperature less than about 100° C. The composite comprises a plurality of superimposed carbon and/or carbonaceous fabric embedded within a thermoplastic resin. The resin comprises about 70 to 95% by weight of polyvinyl chloride, about 5 to 30% by weight of a halogenated polyvinyl chloride. Up to about 2% by weight of a heat stabilizer may be added to the resin, if desired.

The thickness of the composite can be modified by the addition of fabrics, building up of the thermoplastic or the addition of a separate thermoplastic layer between the fabric layers.

The thermoplastic can also contain up to about 15% by weight of impact modifiers.

There are also provided orthotic and prothesis devices which can be prepared with the composite of the invention.

It is a general object of the invention to provide a light weight composite for use in orthotics and/or prosthesis devices.

It is a further object of the invention to provide orthotic and prosthesis devices which can be used without causing skin irritation and which can easily be formed for individual use.

It is still another further objection of the invention to provide a prosthesis device which can be easily fabricated and adjusted without using costly ovens for adjustments.

It is also an object of the invention to provided a thin durable thermoplastic composite which can be deformed in hot water.

For a better understanding of the invention, reference is made for purposes of exemplification only, to the accompanying drawing.

DESCRIPTION OF THE PREFERRED EMBODIMENTS

Figure 1:
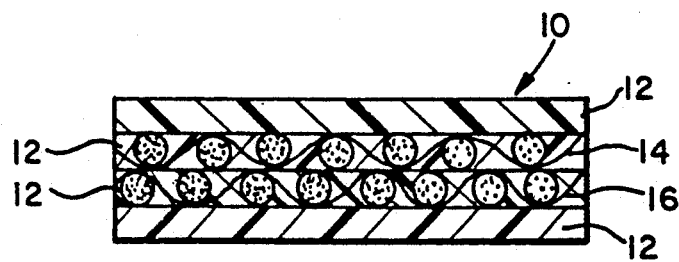
FIG. 1 is a cross-sectional view of one form of composite of the invention.

With reference to FIG. 1, there is shown a fabric reinforced composite 10 which comprises two carbon or carbonaceous woven fabrics 14 and 16 that are embedded in a thermoplastic resin 12 of the invention. The thermoplastic resin comprises about 70 to 95% by weight of polyvinyl chloride, preferably about 80 to 90% by weight, and about 5 to 30% by weight of a halogenated polyvinyl chloride, preferably about 10 to 20% by weight. Preferably the resin contains up to about 2% by weight of a heat stabilizer, preferably up to about 1% by weight.

The composite of FIG. 1 can be prepared by compressing together a prepreg layer of the fabric 14 and a prepreg layer of the fabric 16 at a suitable softening temperature to cause adhesion of the layers.

Figure 2:
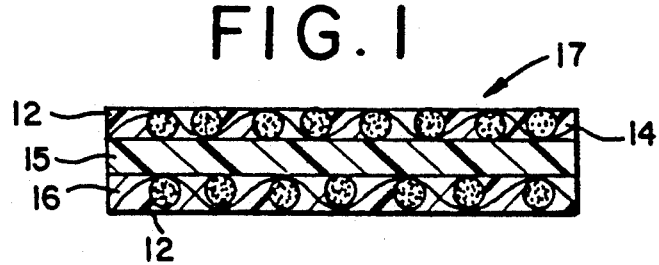
FIG. 2 is a cross-sectional view of another form of composite of the invention.

FIG. 2 illustrates a composite which is formed with a first layer of a carbon or carbonaceous fabric 14 embedded within a thermoplastic resin 12. A second layer of a carbon or carbonaceous fabric 16 embedded within a thermoplastic resin, 12 is separated from the first layer by an intermediate thermoplastic layer 15.

The composite of FIG. 2 can be prepared by compressing together a prepreg layer of fabric 14 and a prepreg layer of fabric 16 with a suitable thermoplastic layer 15 therebetween at a suitable softening temperature to cause adhesion of the layers. Adhesion promoters may be employed depending upon the type of intermediate thermoplastic layer.

The halogenated polyvinyl chloride used in the formation of the composite of the invention is preferably chlorinated polyvinyl chloride although fluorinated polyvinyl chloride would yield a similar composite The chlorine content is generally about 56.8%. An increase of the chlorine content to about 65% increases the heat deflection temperature.

The use of the halogenated polyvinyl chloride in the composite permits forming of the composite by immersion in hot water. It is critical in the invention that the composite is deformable under a temperature of 100° C. Accordingly, an orthotic can be formed without the use of ovens and very high temperatures.

The heat stabilizers which may be used in the invention include sulfur containing organotin compounds derived from betamercaptopropionic acid, dioctytinbis(isooctylthioglycolate), butyltin mercaptide, methyltin mercaptide, tin carboxylate, zinc, barium or cadmium carboxylate, calcium or zinc stearate, lead sulfate, lead phosphite, lead stearate, calcium stearate, 2-phenylindole, and the like.

The intermediate thermoplastic layer may comprise any thermoplastic resin which is capable of deforming at a temperature below about 100° C. (212° F.). A further requirement is that the thermoplastic resin be capable of forming a laminate with the fabric containing layers either alone or through use of adhesion promoters. The intermediate layer is useful to build-up the thickness of the composite.

Suitable thermoplastic resins which may be used as the intermediate layer include polyvinyl alcohol, polyvinyl chloride, polyvinylidene chloride, polystyrene, styrene copolymers, polyolefins, and the like.

A greater impact resistant composite may be prepared by incorporating into the prepreg an impact resistant elastomer in an amount up to about 15% by weight of the composite while still maintaining the characteristic of the composite being reformable at a temperature of less than 100° C. The elastomer is added to the polyvinyl chloride-halogenated polyvinyl chloride when prepared using a melt of the polymers. Suitable impact resistant elastomers include ethylene-vinyl acetate copolymer, ethylene-vinyl acetate, vinyl chloride copolymer, chlorinated polyethylene, acrylonitrile - butadiene - styrene terpolymer, and the like.

The precursor stabilized acrylic filaments which are advantageously utilized in preparing the carbon and carbonaceous fibrous materials of the invention are selected from the group consisting of acrylonitrile homopolymers, acrylonitrile copolymers and acrylonitrile terpolymers.

The copolymers and terpolymers preferably contain at least about 85 mole percent of acrylic units, preferably acrylonitrile units, and up to 15 mole percent of one or more monovinyl units selected from the group consisting of styrene, methylacrylate, methyl methacrylate, vinyl chloride, vinylidene chloride, vinyl pyridene, and the like which copolymerized with the acrylic units.

The carbon and carbonaceous fiber material which is utilized in the composite structures of this invention may be classified into three groups depending upon the particular use and the environment that the structures in which they are incorporated are placed.

In a first group, the non-flammable carbonaceous fibers are non-electrically conductive as utilized in the present invention relates to a resistance of greater than $10^7$ ohms per inch on a 6K tow formed from precursor fibers having a diameter of about 7 to 20 microns.

When the precursor fiber is an acrylic fiber it has been found that a nitrogen content of 18.8% or more results in a nonconductive fiber.

In a second group, the non-flammable non-linear carbonaceous fibers are classified as being partially electrically conductive (i.e., having low conductivity) and have a carbon content of less than 85%. Low conductivity means that a 6K tow of fibers has a resistance of about $10^7$ to $10^4$ ohms per inch. Preferably, the carbonaceous fibers are derived from stabilized acrylic fibers and possesses a percentage nitrogen content of from about 10 to 20% for the case of a copolymer acrylic fiber, more preferably from about 16 to 18%, and up to about a maximum content of about 35% for a terpolymer acrylic fiber.

In a third group are the fibers having a carbon content of at least 85%. These fibers are characterized as being highly conductive. That is, the resistance is less than 10 ohms per inch.

The fibers of this invention may be used in substantially any desired fabricated form which will depend on the purpose for which the composite is to be used.

The fibers can be in the form of a knitted cloth, for example, plain jersey knit, interlock, ribbed, cross float jersey knit or weft knit, or woven into a fabric, for example of plain weave, satin weave, twill weave, basket weave, and the like.

The carbon and carbonaceous fiber cloths are both commercially available. The carbonaceous and carbon fiber cloths can be obtained from Mutual Industries, Inc., Philadelphia, PA.

Figure 3:
FIG. 3 is a side view of an orthotic prepared with the composite of FIG. 1.

In FIG. 3 there is shown a shoe insert 20 which is an arch support prepared from the laminate of FIG. 1.

The thickness of the insert 20 is about 116 to about ¼ inch. The insert can be easily cut into a desired size and shape and then manipulated by placing the insert 20 into hot water. The hot water insert can be readily handled with gloves or a cloth since the temperature need not exceed 100° C. for the insert to be deformable.

Figures 4, 4A:
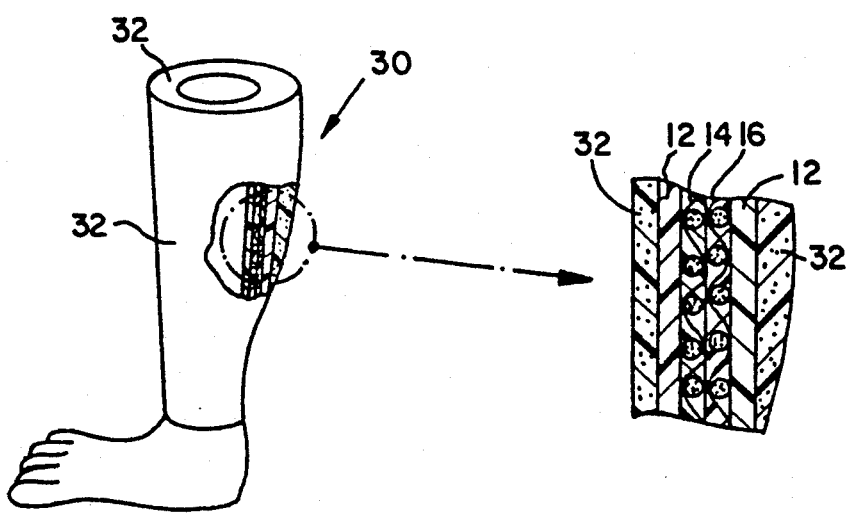
FIG. 4 is a partial cross sectional view of a prothesis prepared with a composite of the invention.

In FIG. 4 there is illustrated a leg prosthesis 30 formed from the laminate 10 of FIG. 1. However, there may be an outside layer of a thermoplastic resin having a softening temperature below 100° C. For example, the outer layers 32 may comprise polyvinyl chloride with a pigment or dye so as to produce a flesh color.

Conventional hot pressing and hot stamping techniques can be employed to produce such laminated articles, regardless of whether they are produced directly from resin-impregnated textiles without prior fusion of the impregnant, or indirectly from prepregs wherein the impregnant has already been fused. When hot pressing is employed, a plurality of the fibrous textile materials to be laminated are laid up one upon another on a suitably shaped mold and formed into a desired shape under a pressure and at a temperature sufficiently elevated to cause the resin-impregnant to fuse (or re-fuse) and bond those materials into a single body. The melt-formed shape is then cooled under confining pressures to a temperature below the melting point of the resin. The composite article formed in this manner may then be trimmed and machined into a desired final product. Alternatively, the fibrous textile materials to be laminated may be cut and fitted to the mold contours and the article molded directly from the blanks. When hot stamping is employed, the procedure is similar except that a plurality of the fibrous textile materials are laid up one upon another, heated at a temperature sufficiently elevated to cause the resin impregnant to fuse (or re-fuse), and then subjected to a pressure sufficient to bond them into a single body of desired shape as they are cooled to a temperature below the melting point of the resin.

Pressures of from about 200 psi. to about 2000 psi, are generally sufficient to produce the desired laminate, regardless of whether hot pressing or hot stamping techniques are employed. The temperature employed will depend upon the particular resin employed.

A further process to prepare the composite is to stack the carbon or graphitic cloths in a mold. Pour a melt of polyvinyl chloride with or without a impact resistance agent. Apply pressure so as to permeate the melt through the stack. Pour a melt comprising a halogenated polyvinyl chloride and a heat stabilizer with or without an impact resistance agent and then applying pressure to form the composite.

A preferred process of the invention comprises the steps of placing at least one carbon or carbonaceous woven or knitted fabric in a mold, coating the fabric with a mixture of polyvinyl chloride in an amount of about 70 to 95% by weight and chlorinated polyvinyl chloride in an amount of about 5 to 30% by weight to form a prepreg. Cutting the prepreg to form a plurality of layers. Stacking at least two layers of the prepreg with an intermediate layer of a thermoplastic film. Then applying heat and pressure to form a laminate.

The laminate can be cut to size to form an orthotic or molded into a prosthesis.

The following examples are set forth for purposes of illustration so that those skilled in the art may better understand this invention. It should be understood that they are exemplary only, and should not be construed as limiting this invention in any manner.

EXAMPLE 1

Six linear feet of woven graphitic fabric was inserted into a 14 inch×14 inch polyethylene bag. Three quarts of polyvinyl chloride and one pint of chlorinated polyvinyl chloride were mixed and about one quart was added to the bag. The bag was attached to a vacuum. The bag was rolled to distribute the resin and to wet out the fabric.

The fabric was then removed from the bag and two cuts of 12 inch×12 inch of fabric taken. The fabrics were stacked in a compression mold hot melt machine with a 1/16 inch layer of polyvinyl alcohol sheet in between. The machine was heated to 160° C. and the stack compressed at 200 psi to form a composite which could be cut to form a reformable orthoses.

EXAMPLE 2

Two 12 inch×6 inch woven fabric of carbonaceous fibers were in a 12 inch×6 inch×= inch stainless steel mold. The mold is filled with polyvinyl chloride and then compressed in a hot press of the type normally used for preparing films at a temperature of 90° to 110° C. and at a pressure of from 15,000 to 40,000 psig. The mold is cooled and filled with powdered chlorinated polyvinyl chloride and about 1% of butyltin mercaptide as an inhibitor. The mold was again heated to about 90° to 110° C., and a pressure of about 15,000 to 40,000 psig applied.

The composite can be use to make an orthoses.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. An orthotic or prosthesis device consisting of a fabric reinforced thermoplastic composite which is reformable at a temperature less than about 100° C. which comprises:
   a plurality of superimposed carbon or carbonaceous fabric layers embedded within a first thermoplastic resin, said first thermoplastic resin comprising about 70 to 95% by weight of polyvinyl chloride and about 5 to 30% by weight of halogenated polyvinyl chloride which is reformable at a temperature less than about 100° C., and
   a second thermoplastic resin bonded between said fabric reinforced layers and capable of deforming at a temperature below about 100° C., whereby said composite is reformable when heated in hot water.

2. The composite of claim 1 wherein said halogenated polyvinyl chloride is chlorinated polyvinyl chloride.

3. The composite of claim 1 wherein said second thermoplastic resin differs from said first thermoplastic resin.

4. The composite of claim 1 wherein a heat stabilizer is included in said composite.

5. The composite of claim 1 wherein said fabric comprises graphitic fibers.

6. The composite of claim 1 wherein said fabric comprises carbonaceous fibers.

7. The composite of claim 6 wherein said fibers are electrically non-conductive.

8. The composite of claim 1 wherein said thermoplastic resin comprises about 80 to 90% by weight of polyvinyl chloride.

9. The composite of claim 1 having a thickness about 1/16 to ¼ inch.

10. An orthotic or prosthetic device consisting of a fabric reinforced thermoplastic composite which is reformable under a temperature of about 100° C. which comprises:
    a plurality of superimposed graphitic or carbonaceous fabrics embedded within a thermoplastic resin, said thermoplastic resin being reformable at a temperature less than about 100° C. comprising about 80% to 90% by weight polyvinyl chloride, about 10 to 20% chlorinated polyvinyl chloride and up to about 1% of a heat stabilizer, and a second heat reformable thermoplastic layer capable of deforming at a temperature below about 100° C. bonded between said embedded fabrics, whereby said composite is reformable when heated in hot water.

11. The orthotic device of claim 1 which is an arch support.

* * * * *